United States Patent
Lang (12) United States Patent (10) Patent No.: US 6,576,012 B2
Lang (45) Date of Patent: Jun. 10, 2003

(54) BINOCULAR LENS SYSTEMS

(75) Inventor: Alan J. Lang, Long Beach, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 09/819,436

(22) Filed: Mar. 28, 2001

(65) Prior Publication Data

US 2002/0143394 A1 Oct. 3, 2002

(51) Int. Cl.$^7$ .................................................. A61F 2/16
(52) U.S. Cl. .................................. 623/6.28; 623/6.32
(58) Field of Search ........................... 623/6.23, 6.24, 623/6.25–6.36

(56) References Cited

U.S. PATENT DOCUMENTS

| | | |
|---|---|---|
| 1,483,509 A | 2/1924 | Bugbee |
| 2,129,305 A | 9/1938 | Feinbloom |
| 2,274,142 A | 2/1942 | Houchin |
| 2,405,989 A | 6/1946 | Beach |
| 2,511,517 A | 6/1950 | Spiegel |
| 3,031,927 A | 5/1962 | Wesley |
| 3,034,403 A | 5/1962 | Neefe |
| RE25,286 E | 11/1962 | de Carle |
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,693,301 A | 9/1972 | Lemaltre |
| 3,922,728 A | 12/1975 | Krasnov |
| 3,932,148 A | 1/1976 | Krewalk, Sr. |
| 4,055,378 A | 10/1977 | Feneberg et al. |
| 4,062,629 A | 12/1977 | Winthrop |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Gullino et al. |

(List continued on next page.)

FOREIGN PATENT DOCUMENTS

| | | |
|---|---|---|
| AU | 3225789 | 10/1989 |
| DE | 2702117 | 7/1978 |

(List continued on next page.)

OTHER PUBLICATIONS

Video Tape "New Elliptical Acco. IOL for Cataract Surgery" Shown at ASCRS Symposium on Apr. 10, 1999 (Video Enclosed).

(List continued on next page.)

Primary Examiner—Corrine McDermott
Assistant Examiner—Hieu Phan
(74) Attorney, Agent, or Firm—Stout, Uxa, Buyan & Mullins, LLP; Frank J. Uxa; Peter Jon Gluck (57) ABSTRACT

An binocular lens system for improving the vision of a patient including first and second ophthalmic lenses. Each of these lenses is adapted for implantation in an eye or to be disposed on or in the cornea. The first lens has a first baseline diopter power for distance vision correction and the second ophthalmic lens has a second baseline diopter power for other than distance vision correction. The ophthalmic lenses may be intraocular lenses which are implanted in the eyes of a patient or has natural lenses or following removal of the natural lenses.

38 Claims, 7 Drawing Sheets

U.S. PATENT DOCUMENTS

| | | | |
|---|---|---|---|
| 4,253,199 A | 3/1981 | Banko | |
| 4,254,509 A | 3/1981 | Tennant | |
| 4,274,717 A | 6/1981 | Davenport | |
| 4,307,945 A | 12/1981 | Kitchen et al. | |
| 4,315,673 A | 2/1982 | Guilino et al. | |
| 4,316,293 A | 2/1982 | Bayers | |
| 4,338,005 A | 7/1982 | Cohen | |
| 4,340,283 A | 7/1982 | Cohen | |
| 4,370,760 A | 2/1983 | Kelman | |
| 4,377,329 A | 3/1983 | Poler | |
| 4,402,579 A | 9/1983 | Poler | |
| 4,404,694 A | 9/1983 | Kelman | |
| 4,409,691 A | 10/1983 | Levy | |
| 4,418,991 A | 12/1983 | Breger | |
| 4,476,591 A | 10/1984 | Arnott | |
| 4,504,982 A | 3/1985 | Burk | |
| 4,551,864 A | 11/1985 | Akhavi | |
| 4,560,383 A | 12/1985 | Leiske | |
| 4,573,775 A | 3/1986 | Bayshore | |
| 4,580,882 A | 4/1986 | Nuchman et al. | |
| 4,596,578 A | 6/1986 | Kelman | |
| 4,618,228 A | 10/1986 | Baron et al. | |
| 4,618,229 A | 10/1986 | Jacobstein et al. | |
| 4,636,049 A | 1/1987 | Blaker | |
| 4,636,211 A | 1/1987 | Nielsen et al. | |
| 4,637,697 A | 1/1987 | Freeman | |
| 4,641,934 A | 2/1987 | Freeman | |
| 4,676,792 A | 6/1987 | Praeger | |
| 4,687,484 A | 8/1987 | Kaplan | |
| 4,693,572 A | 9/1987 | Tsnetaki et al. | |
| RE32,525 E | 10/1987 | Pannu | |
| 4,702,244 A | 10/1987 | Mazzocco | |
| 4,704,016 A | 11/1987 | de Carle | |
| 4,720,286 A | 1/1988 | Bailey et al. | |
| 4,725,278 A | 2/1988 | Shearing | |
| 4,752,123 A | 6/1988 | Blaker | |
| 4,759,762 A | 7/1988 | Grendahl | |
| 4,769,033 A | 9/1988 | Nordan | |
| 4,790,847 A | 12/1988 | Woods | |
| 4,813,955 A | 3/1989 | Achatz et al. | |
| 4,830,481 A | 5/1989 | Futhey et al. | |
| 4,842,601 A | 6/1989 | Smith | |
| 4,881,804 A | 11/1989 | Cohen | |
| 4,888,012 A | 12/1989 | Horn et al. | |
| 4,888,015 A | 12/1989 | Domino | |
| 4,890,912 A | 1/1990 | Visser | |
| 4,890,913 A | 1/1990 | de Carle | |
| 4,892,543 A | 1/1990 | Turley | |
| 4,898,461 A | 2/1990 | Portney | |
| 4,906,246 A | 3/1990 | Grendahl | |
| 4,917,681 A | 4/1990 | Nordan | |
| 4,919,663 A | 4/1990 | Grendahl | |
| 4,921,496 A | 5/1990 | Grendahl | |
| 4,923,296 A | 5/1990 | Erickson | |
| 4,932,966 A | 6/1990 | Christie et al. | |
| 4,932,968 A | 6/1990 | Caldwell et al. | |
| 4,938,583 A | 7/1990 | Miller | |
| 4,955,902 A | 9/1990 | Kelman | |
| 4,976,534 A | 12/1990 | Miege et al. | |
| 4,976,732 A | 12/1990 | Vorosmarthy | |
| 4,990,159 A | 2/1991 | Kraff | |
| 4,994,082 A | 2/1991 | Richards et al. | |
| 5,000,559 A | 3/1991 | Takahashi et al. | |
| 5,002,382 A * | 3/1991 | Seidner | 351/161 |
| 5,019,098 A * | 5/1991 | Mercier | 351/161 |
| 5,019,099 A | 5/1991 | Nordan | |
| 5,047,052 A | 9/1991 | Dubroff | |
| 5,071,432 A | 12/1991 | Baikoff | |
| 5,074,877 A * | 12/1991 | Nordan | 623/6.24 |
| 5,089,024 A | 2/1992 | Christie et al. | |
| 5,096,285 A | 3/1992 | Silberman | |
| 5,112,351 A | 5/1992 | Christie et al. | |
| 5,147,397 A | 9/1992 | Christ et al. | |
| 5,158,572 A | 10/1992 | Nielsen | |
| 5,166,711 A | 11/1992 | Portney | |
| 5,166,712 A | 11/1992 | Portney | |
| 5,171,266 A | 12/1992 | Wiley et al. | |
| 5,173,723 A | 12/1992 | Volk | |
| 5,192,317 A | 3/1993 | Kalb | |
| 5,192,318 A | 3/1993 | Schneider | |
| 5,201,762 A | 4/1993 | Hauber | |
| 5,225,858 A | 7/1993 | Portney | |
| 5,236,452 A * | 8/1993 | Nordan | 623/6.24 |
| 5,258,025 A | 11/1993 | Fedorov et al. | |
| 5,260,727 A | 11/1993 | Oksman et al. | |
| 5,270,744 A | 12/1993 | Portney | |
| 5,275,623 A | 1/1994 | Sarfarazi | |
| 5,354,335 A | 10/1994 | Lipshitz et al. | |
| 5,443,506 A | 8/1995 | Garabet | |
| 5,476,514 A | 12/1995 | Cumming | |
| 5,480,428 A | 1/1996 | Fedorov et al. | |
| 5,489,302 A | 2/1996 | Skottun | |
| 5,496,366 A | 3/1996 | Cumming | |
| 5,521,656 A | 5/1996 | Portney | |
| 5,549,760 A | 8/1996 | Becker | |
| 5,562,731 A | 10/1996 | Cumming | |
| 5,574,518 A | 11/1996 | Mercure | |
| 5,578,081 A | 11/1996 | McDonald | |
| 5,607,472 A | 3/1997 | Thompson | |
| 5,628,795 A | 5/1997 | Langerman | |
| 5,628,796 A | 5/1997 | Suzuki | |
| 5,652,014 A | 7/1997 | Galin et al. | |
| 5,652,638 A | 7/1997 | Roffman et al. | |
| 5,657,108 A | 8/1997 | Portney | |
| 5,674,282 A | 10/1997 | Cumming | |
| 5,682,223 A | 10/1997 | Menezes et al. | |
| 5,684,560 A | 11/1997 | Roffman et al. | |
| 5,702,440 A | 12/1997 | Portney | |
| 5,766,244 A | 6/1998 | Binder | |
| 5,769,890 A | 6/1998 | McDonald | |
| 5,776,191 A | 7/1998 | Mazzocco | |
| 5,800,533 A | 9/1998 | Eggleston et al. | |
| 5,814,103 A | 9/1998 | Lipshitz et al. | |
| 5,843,188 A | 12/1998 | McDonald | |
| 5,847,802 A | 12/1998 | Menezes et al. | |
| 5,864,378 A | 1/1999 | Portney | |
| 5,876,442 A | 3/1999 | Lipshitz et al. | |
| 5,898,473 A | 4/1999 | Seidner et al. | |
| 5,929,969 A | 7/1999 | Roffman | |
| 6,013,101 A | 1/2000 | Israel | |
| 6,096,078 A | 8/2000 | McDonald | |
| 6,110,202 A | 8/2000 | Barraquer et al. | |
| 6,176,878 B1 | 1/2001 | Gwon et al. | |
| 6,197,058 B1 | 3/2001 | Portney | |
| 6,217,612 B1 | 4/2001 | Woods | |
| 6,231,603 B1 * | 5/2001 | Lang et al. | 623/6.24 |

FOREIGN PATENT DOCUMENTS

| | | |
|---|---|---|
| DE | 3246306 | 6/1984 |
| EP | 0246216 | 11/1987 |
| EP | 0329981 | 8/1989 |
| EP | 0337390 | 10/1989 |
| EP | 0342895 | 11/1989 |
| EP | 0351471 | 1/1990 |
| EP | 0480748 | 4/1992 |
| EP | 0566170 | 10/1993 |
| EP | 0691109 | 1/1996 |
| EP | 0780718 | 6/1997 |
| EP | 0897702 | 2/1999 |
| FR | 2666735 | 3/1992 |
| FR | 0488835 | 6/1992 |

| | | |
|---|---|---|
| FR | 2784575 | 4/2000 |
| GB | 939016 | 10/1963 |
| GB | 2058391 | 4/1981 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |
| WO | 86/03961 | 7/1986 |
| WO | 87/00299 | 1/1987 |
| WO | 87/07496 | 12/1987 |
| WO | 89/02251 | 3/1989 |
| WO | 89/11672 | 11/1989 |
| WO | 91/09336 | 6/1991 |
| WO | 94/16648 | 8/1994 |
| WO | 95/03783 | 2/1995 |
| WO | 96/10968 | 4/1996 |
| WO | 96/15734 | 5/1996 |
| WO | 96/25126 | 8/1996 |
| WO | 97/12272 | 4/1997 |
| WO | 97/43984 | 11/1997 |
| WO | 98/21621 | 5/1998 |
| WO | 98/49594 | 11/1998 |
| WO | 98/56315 | 12/1998 |
| WO | 99/03427 | 1/1999 |
| WO | 99/29266 | 6/1999 |
| WO | 00/46629 | 8/2000 |
| WO | 00/66039 | 11/2000 |
| WO | 01/34067 | 5/2001 |
| ZA | 0888414 | 11/1988 |

OTHER PUBLICATIONS

Partial Program Re: ASCRS Symposium, Showing Video Tape shown between Apr. 10–14, 1999.
Mandell, Contact Lens Practice, 4th Ed.
Holladay et al, J. Cataract Refractive Surg., vol. 14, Jan. 1955.
The Shah Bifocal Intraocular Lens Implant.
Thornton, Color Atlas of Lens Implantation, Accommodation in Pseudophakia, pp. 159–162, 1991.
Amo Specs, Model AC–21B, 1992.
Chrion Vision, Nuvita MA20, 1997.
Menezo et al. J Cataract Refract Surg 24, Aug. 1998.
Fechner et al. J Cataract Refract Surg 24, Jan. 1998.
Jacobi, MD., et al, Arch Opthalmol, vol. 117, pp. 17–23, Jan., 1999.

* cited by examiner

BINOCULAR LENS SYSTEMS

BACKGROUND OF THE INVENTION

This invention relates to binocular lens systems which comprise ophthalmic lenses. The lenses may be adapted for implantation in an eye such as intraocular lenses(IOLS) or adapted to be disposed on or in the cornea such as contact lenses or corneal inlays.

When functioning normally, the natural lens of the eye is somewhat elastic and therefore enables good vision of objects at all distances. However, when the natural lens is removed as a result of disease or injury and replaced with an IOL, the natural ability of the eye to accommodate is lost completely. However, an ability to have adequate vision at different distances without using spectacles can be provided by the IOL which is implanted following removal of the natural lens. To this end, the IOL may be multifocal as shown and described, for example, in Portney U.S. Pat. No. 5,225,858, Roffman et al U.S. Pat. No. 5,448,312 or Menezes et al U.S. Pat. No. 5,682,223. Alternatively, the IOL may be of the type which is accommodating in that it can be moved by the eye itself as shown and described in commonly assigned application Ser. No. 09/532,910 filed Mar. 22, 2000 or monofocal with a depth of focus feature as shown and described in Portney U.S. Pat. No. 5,864,378.

Another approach to overcoming loss of accommodation is to use ophthalmic lenses, such as contact lenses or IOLS, with different optical characteristics for each eye. For example with a system known as monovision one lens has a distance vision correction power and the other lens has a near vision correction power. Another example is shown and described in Roffman et al U.S. Pat. No. 5,485,228. It is also known to implant a distant dominant multifocal IOL in one eye and a near dominant multifocal IOL in the other eye as disclosed in the January 1999 issue of Clinical Sciences by Jacobi et al entitled "Bilateral Implantation of Asymmetrical Diffractive Multifocal Intraocular Lenses," pages 17–23.

Ophthalmic multifocal lenses can also be provided with some depth of focus. This is shown and described, for example, in Portney U.S. Pat. No. 5,225,858 and Roffman et al U.S. Pat. No. 5,684,560.

Whether monovision or multifocal ophthalmic lenses are employed, nighttime images may not be the same for both eyes and/or possess halos as when the headlights of an oncoming vehicle are observed. This can significantly reduce the ability of the observer to identify and locate objects near the headlights. For example, halos tend to be created when the patient views a distant object through the near vision portion of a multifocal lens, and the greater the add power, the more perceptible is the halo.

For example, this is shown and described in commonly assigned application Ser. No. 09/302,977 filed on Apr. 30, 1999. This application discloses a reduced add power multifocal IOL which reduces the effects of halos. This reduced add power IOL is implanted in a phakic eye in which the natural lens has lost some degree of accommodation, i.e. in partially presbyopic eyes.

The disclosure of each of the patent applications and patents identified herein is incorporated in its entirety herein by reference.

SUMMARY OF THE INVENTION

New binocular ophthalmic lens systems have been discovered. The present lens systems provide a combined effect of enhancing distance, intermediate and near visual function. In particular, the lens systems are very effective in enhancing intermediate vision, for example, relative to systems including two identical multifocal lenses. Near vision comparable to that of the "identical lens" system is provided by the present lens systems for both the absolute presbyope in a phakic application and in a pseudophakic application. Near vision preferably is enhanced for the earlier presbyope in the phakic application compared to the "identical lens" systems. The size and/or intensity of multifocal halos preferably is reduced with the present lens systems. Other important advantages are obtained.

In general, the present lens systems comprise two lenses. The ophthalmic lens systems of this invention may include first and second lenses for use with, for example, in or on, first and second eyes of a patient, respectively. Each of the first and second lenses has more than one vision correction power and is therefore multifocal. Although this invention is particularly adapted for IOLS, it is also applicable to lenses which can be disposed on or in the cornea such as contact lenses and corneal inlays.

One lens, the first lens, has a first baseline diopter power for distance vision correction, and preferably provides the best image quality for distance or distant objects. The other lens, the second lens, has a second baseline diopter power for other than distance vision correction and preferably has a baseline diopter power which is more myopic than the first diopter power, more preferably which is for intermediate vision correction. For example, the second baseline power may be selected such that the distance refraction of the subject in whose eyes the present lenses are placed is about 1.5 diopters more myopic than that of the first lens.

Baseline diopter power is the optical power which provides best visual acuity at a given or targeted distance.

The first lens is biased for distance vision or distance biased. This may be accomplished, for example, by configuring the first lens so that the best visual acuity provided by the lens is for distant objects, for example, objects at infinity. The first lens provides better visual acuity for objects at infinity than the second lens. Preferably, the first lens substantially optimizes visual acuity from distance to intermediate distances. The first lens has a power including a maximum add power which preferably is less than the add power for full near vision correction for the patient. Advantageously, the maximum add power of the first lens is no greater than about an add power for intermediate vision. The power of the first lens preferably varies from about the power for distance vision to the add power for intermediate vision. For example, the maximum add power of the first lens may be no more than about 1.5 diopters or about 1.75 diopters. All of the add powers set forth herein are in the spectacle plane. The first lens preferably has a power including a power required for distance vision correction for the patient.

The second lens preferably is biased for intermediate vision. This may be accomplished, for example, by configuring the second lens so that the best visual acuity provided by the second lens is for objects at intermediate distances. Alternatively, or in addition thereto, the second lens provides better visual acuity from intermediate to near distances than the first lens. Preferably, the second lens enhances visual acuity from intermediate to near distances. At least one of the first lens and the second lens preferably has a power including an intermediate add power for intermediate vision correction for the patient and a maximum add power which is less than the add power required for full near vision correction for the patient. More preferably, the maximum add power for the second lens, and still more preferably for both the first and second lenses, is less than the add power required for full near vision correction for the patient. The second lens advantageously has a maximum add power of any region of the second lens no greater than about the intermediate add power.

The lenses can be made to have the relatively larger ranges of vision in various ways. For example, this can be accomplished by appropriately splitting the light between distance, intermediate and near. Thus, the second lens may focus sufficient light to a near focus region so as to contribute to the second lens providing enhanced vision and better visual acuity from intermediate to near distance.

Alternatively or in addition thereto, the depth of focus of the zone or zones of the lens which provide intermediate vision correction may be appropriately increased to provide the second lens with enhanced vision characteristics from intermediate to near distances. This may be accomplished, for example, by controlling the aspheric surface design of the lenses. More specifically, the first and second lenses may each have a zone with an add power for intermediate vision correction with such zone having optical aberrations which increase the depth of focus of such zone. In one preferred embodiment, such zones extend radially outwardly and have progressively changing add powers as the zones extend radially outwardly.

The add powers of the first lens and the second lens preferably are reduced over what they would be if the lens had the full add power required for near vision correction. The reduced add powers significantly reduce the size and/or intensity of multifocal lens halos, such as those halos which occur in any eye because of the relatively large add power component, e.g., full near vision add power, found in many multifocal lens designs.

In the interest of keeping the add powers low while providing adequate vision quality, preferably the maximum add power of the first lens is no greater than about the power required for intermediate vision correction and the maximum add power of the second lens is less than the full add power for near vision correction. By way of example, the maximum add power for the first lens may be from about 0.5 diopter to about 1.75 diopters and is preferably from about 1 diopter to about 1.5 diopters. The full or complete near vision correction typically is in a range of about 2.0 diopters or about 2.5 diopters to about 3.0 or more diopters of add power. Thus, the maximum add power of the second lens preferably is less than about 2.5 diopters of add power, more preferably less than about 2.0 diopters of add power.

The first and second lenses are adapted to provide some depth of focus. The first and second lenses preferably provide some depth of focus toward intermediate vision correction.

Each of the first and second lenses has an optical axis. Preferably the power of the first lens is different at a plurality of locations radially outwardly of the optical axis of the first lens, and the power of the second lens is different at a plurality of locations radially outwardly of the optical axis of the second lens.

Viewed from a different perspective, the power of each of the first and second lenses changes along a power curve, for example, in a radially outward direction from the associated optical axis. The power curve for the first lens is different from the power curve for the second lens. In one useful embodiment of the present invention, the power curve of the first lens is substantially similar to the power curve of the second lens except for the difference between the first baseline power and the second baseline power. The power curve of the first lens may at least contribute to the first lens having good visual acuity from distance to intermediate distances and the power curve of the second lens may at least contribute to the second lens having good visual acuity from intermediate to near distances. The first lens may have a power which varies from about the power required for far vision correction to about a power required for intermediate vision correction. The second lens may have a power which varies from a power required for intermediate vision correction or somewhat below intermediate vision correction to the power required for greater than intermediate vision correction, preferably, however, less than a power required for full near vision correction.

In one preferred embodiment, the first lens has first, second and third optical zones arranged radially with respect to the optical axis of the first lens with the second zone being intermediate or between the first and third zones and having a greater add power than either of the first and third zones. The second lens has first, second and third optical zones arranged radially with respect to the optical axis of the second lens with the second zone being intermediate or between the first and third zones and having a greater add power than either of the first and third zones of the second lens.

Although the zones can be of various configurations, they are preferably substantially annular and substantially concentric. Preferably, there are at least two zones. Still more preferably, there are three or five of the zones with the innermost and outermost of the zones of the first lens having a power for far vision correction and the innermost and outermost of the zones of the second lens having a power other than distance vision correction, preferably for substantially intermediate vision correction.

The power in a radial direction can change either gradually or abruptly. In one form of the invention, each of the second zones has a power which is substantially constant.

IOLS constructed in accordance with this invention may be implanted following removal of the natural lenses or in phakic eyes, for example, phakic eyes having some residual accommodation.

According to one aspect of the method of this invention, first and second multifocal ophthalmic lenses having different baseline diopter powers are placed on or in the eyes, respectively, of the patient. The first lens has a first baseline diopter power for distance vision correction and provides better visual acuity for objects at infinity than the second lens. The second lens has a second baseline diopter power for other than distance vision correction, preferably for about intermediate vision correction, and provides better visual acuity for from intermediate to near distances than the first lens. The maximum add power of the second lens preferably is less than the add power required for near vision correction. In one embodiment, the second baseline power is more myopic than the first baseline power. Preferably the ophthalmic lenses are IOLs and the step of placing includes implanting the first and second lenses in the eyes, respectively, of the patient, for example, with the patient's natural lenses in place or after removal of the patient's natural lenses.

According to another feature of the method of this invention, first and second multifocal ophthalmic lenses having different baseline diopter powers are placed on or implanted in the eyes, respectively, of a patient, without removing the patient's natural lenses. Each of the first and second lenses has a power which changes along a power curve, with the power curve of the first lens being substantially similar to the power curve of the second lens.

Although the first and second lenses of the present inventions may be contacts or corneal inlays, the features of this invention are particularly adapted for IOLS which can be implanted, respectively, in the eyes of the patient.

Any and all features described herein and combinations of such features are included within the scope of the present invention provided that the features of any such combination are not mutually inconsistent.

The invention, together with additional features and advantages thereof, may best be understood by reference to the following description taken in connection with the accompanying illustrative drawings.

DESCRIPTION OF THE PREFERRED EMBODIMENTS

Figure 1:
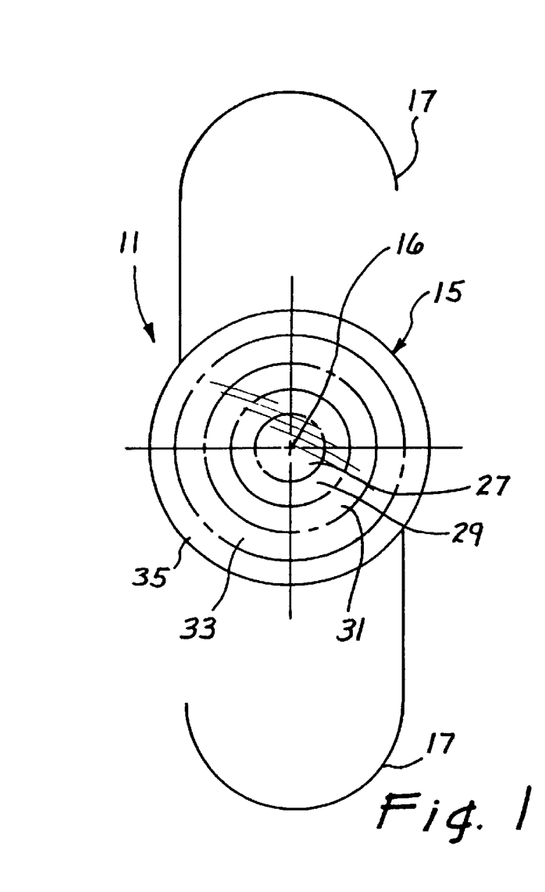
FIG. 1 is a somewhat schematic elevational view of another embodiment of an IOL constructed in accordance with this invention which is particularly adapted for distance-to-intermediate vision.
Figure 2:
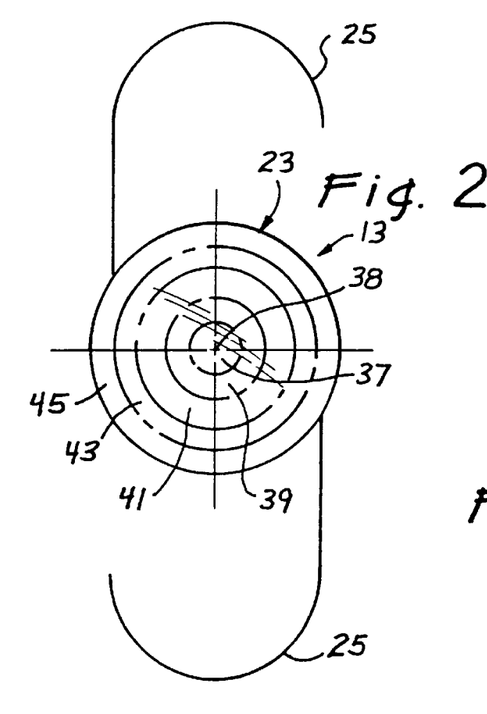
FIG. 2 is a view similar to FIG. 1 of one embodiment of an IOL constructed in accordance with this invention which is particularly adapted for intermediate-to-near-vision.

FIG. 1 shows a distance-to-intermediate multifocal IOL 11 and FIG. 2 shows an intermediate-to-near multifocal IOL 13 which together with the IOL 11 form a lens pair or ophthalmic lens system for enhancing the vision of a patient. The IOL 11 includes a multifocal lens body or optic 15 an optical axis 16 and having powers for a vision correction as described more fully hereinbelow. The IOL 11 also includes generally radially extending fixation members 17 which, in this embodiment, are secured to the lens body 15.

A variety of configurations can be employed for the fixation members 17 in order to provide for effective fixation of the IOL 11 in the eye. If the IOL 11 is to be implanted following removal of the natural lens from the eye, then any of those configurations known in the art for that purpose may be employed. On the other hand, if the IOL 11 is to be implanted without removal of the natural lens from the eye, then the fixation members 17 should be of a configuration and construction which will allow the IOL 11 and the natural lens of the eye to usefully coexist in the eye. In that regard, any of the configurations shown by way of example in commonly assigned application Ser. No. 09/302,977, filed on Apr. 30, 1999 may be employed.

Figure 4:
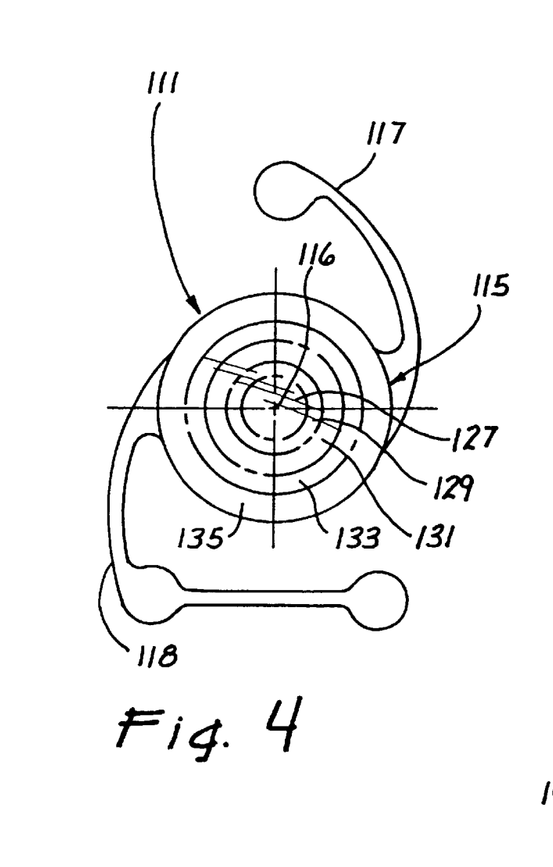
FIG. 4 is a somewhat schematic elevational view of another embodiment of an IOL constructed in accordance with this invention which is particularly adapted for distance-to-intermediate vision.
Figure 5:
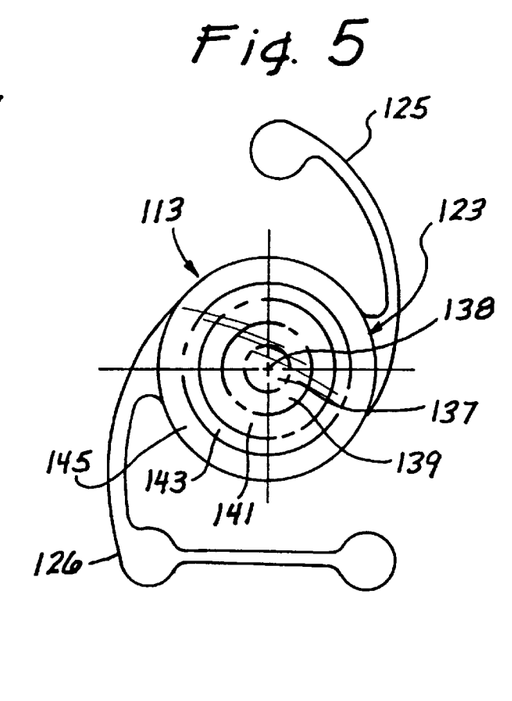
FIG. 5 is a view similar to FIG. 4 of another embodiment of an IOL constructed in accordance with this invention which is particularly adapted for intermediate-to-near vision.
Figure 6:
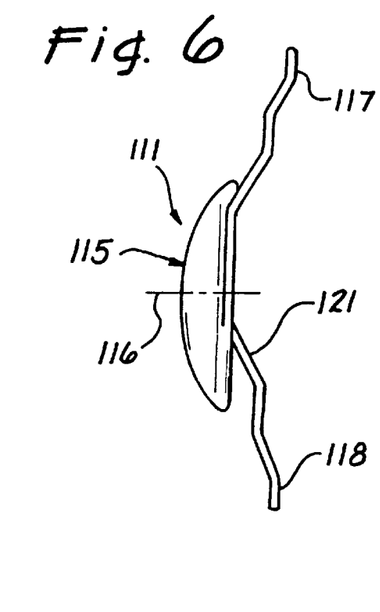
FIG. 6 is a side elevational view of the IOL of FIG. 4.

The IOLs 111 and 113, shown in FIGS. 4 to 6 are very useful when implanted without removal of the natural lenses. Such IOLs are described further hereinafter.

The fixation members 17 may be made of materials of construction, such as polymeric materials, for example, acrylic, polypropylene, silicone, polymethylmethacrylate and the like, many of which are conventionally used in fixation members. In the embodiment shown each of the fixation members 17 has the form shown by way of example in FIGS. 1 and 3, and this adapts the IOL 11 for implantation in the capsular bag of the eye after removal of the natural lens.

The lens body 15 may be constructed of rigid biocompatible materials such as polymethylmethacrylate (PMMA), or flexible, deformable materials, such as silicone polymeric material, acrylic polymeric material, hydrogel polymeric material and the like, which enable the lens body to be rolled or folded before insertion through a small incision into the eye. Although the lens body 15 shown in FIG. 1 is a refractive lens body, it may be diffractive if desired.

Figure 3:
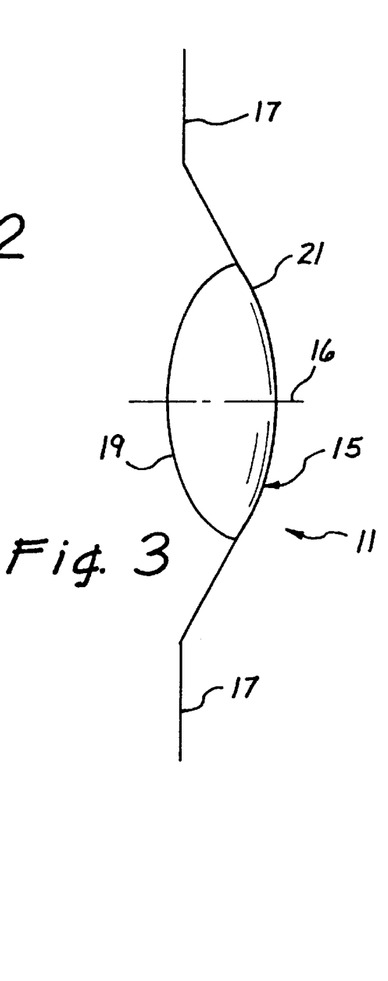
FIG. 3 is a side elevational view of the IOL of FIG. 1.

As shown in FIG. 3, the lens body 15 has a convex anterior surface 19 and a convex posterior surface 21; however, these configurations are merely illustrative. Although the vision correction power may be placed on either of the surfaces 19 or 21, in this embodiment, the anterior surface 19 is appropriately shaped to provide the desired vision correction powers.

The IOL 13 similarly has a multifocal lens body 23 and fixation members 25 suitably joined to the lens body 23. The optical characteristics, and in particular the baseline diopter powers, of the lens bodies 15 and 23 are different as described more specifically herein below. However, except for the optical characteristics of the lens bodies 15 and 23, the IOLs 11 and 13 may be identical.

With respect to optical characteristics, it can be seen from FIG. 1 that the IOL 11 has a central zone 27 and additional optical zones 29, 31, 33 and 35. In this embodiment, the central zone 27 is circular and the lens body 15 has a circular outer periphery. Also, in this embodiment, the additional optical zones 29, 31, 33 and 35 are annular and concentric with the central zone 27, and all of these zones are centered on the optical axis 16.

Figure 7:
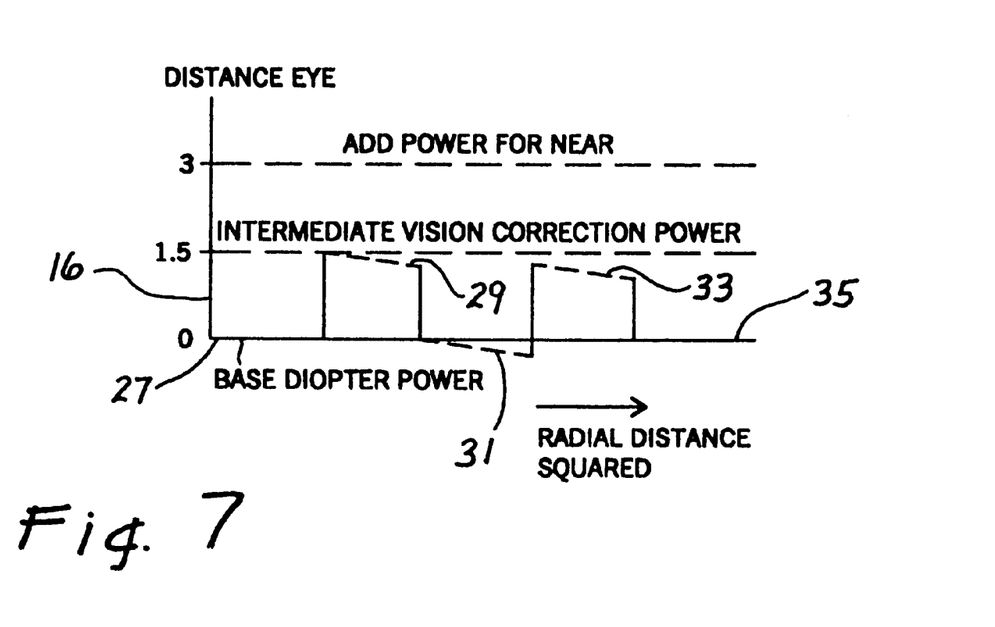
FIG. 7 is a plot of add power of the IOL of FIG. 1 versus radial distance squared from the optical axis of that IOL.
Figure 8:
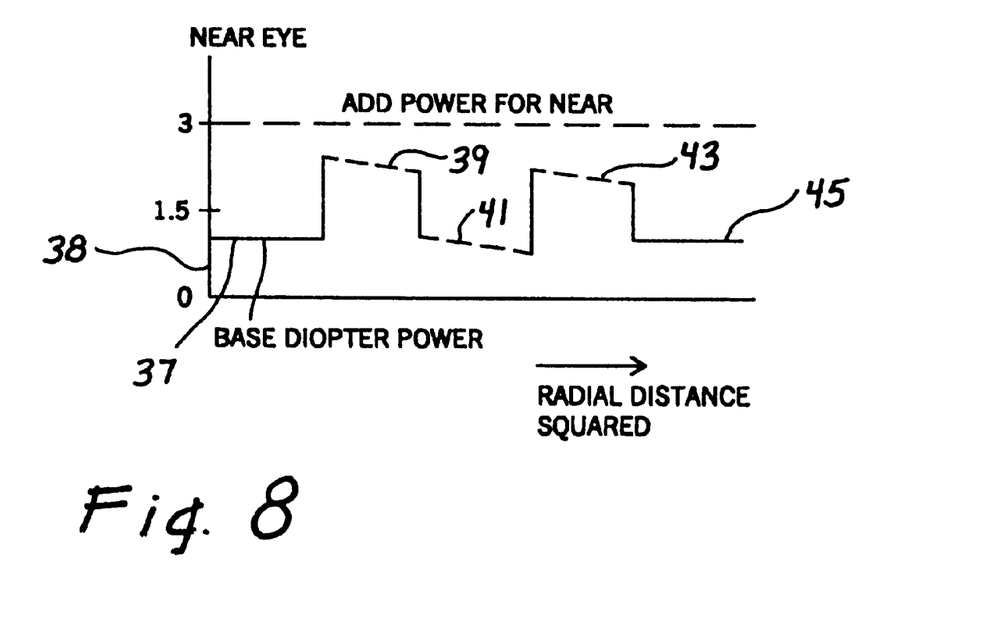
FIG. 8 is a plot similar to FIG. 7 for the IOL of FIG. 2.

With reference to FIG. 7, it can be seen that the central zone 27 and the outermost annular zone 35 have a base or baseline diopter power which is the power required by the patient for distance vision correction and is considered as a zero add power. It should also be noted that the diopter power variation shown in FIGS. 7 and 8 is applicable to any point on the surface of the lens bodies 15 and 23, respectively, at a fixed radial distance from the associated optical axes. In other words, the power at any given radial distance from the optical axis 16 is the same, and the power at any given radial distance from the optical axis 38 is the same.

The annular zone 31 has about the first baseline diopter power required for distance vision correction. Although the annular zone 31 could have precisely the power required for distance vision correction, i.e. the first baseline diopter power or zero add power, in this embodiment, the power of the annular zone 31 decreases progressively and slightly from the outer edge of the zone 29 to about the inner edge of the zone 33 to provide spherical aberration correction. Thus, although the optical power of the zone 31 does diminish in a radial outward direction in this fashion, it nevertheless is considered to be about the power needed for far or distance vision correction for the patient. For example, the vision correction power of the zone 31 may decrease from the first baseline diopter power or zero add power to about 0.25 diopter below the first baseline diopter power.

The zones 29 and 33 have greater vision correction power than the zones 27, 31 and 35 and are preferably at or about the power required for intermediate vision correction. In terms of a single power, the power for intermediate vision correction would be halfway between the base diopter power and the add power for near vision correction. By way of example, if the first baseline diopter power is considered to be zero add and the add power for near vision correction is considered to be 3 diopters, then the power for intermediate vision correction would be 1.5 diopters of add power. More broadly, however, the intermediate vision correction power may be taken to embrace a zone of from about 0.5 diopter to about 1.75 diopters and preferably that zone may be from about 1 diopter to about 1.5 diopters. When thus considered, the power of the zones 29 and 33 would all be add powers for intermediate vision correction.

The vision correction power in the zone 29 reduces progressively and slightly in a radial outward direction from an add power for intermediate vision correction such as 1.5 diopters as shown in FIG. 7 to a slightly less add power for intermediate vision correction so as to provide for spherical aberration correction. Again, to correct for spherical aberration, the maximum power of the zone 33 is less than the minimum power of the zone 29 and reduces progressively and slightly in a radial outward direction as shown in FIG. 7. By way of example, the power of the zone 29 may decrease linearly from about 1.5 diopters to about 1.25 diopters and the vision correction power of the zone 33 may reduce linearly in a radial outward direction from about 1.0 diopter to about 0.75 diopter. Thus, all of the powers of the zones 29 and 33 may be considered as add powers for intermediate vision correction. Thus, it can be readily seen from FIG. 7 that the maximum power of any region of the first lens body 15 is no greater than about the power for intermediate vision correction.

The annular areas of the distance correction zones 27, 31 and 35 are intended to be larger than the annular areas of the intermediate power zones 29 and 33. Moreover, there are three of the distance power zones 27, 31 and 35 and only two of the intermediate vision correction zones 29 and 33, although other numbers of these zones may be employed, if desired. Thus, a larger surface of the lens body 15 is dedicated to focusing or directing light to a far focus region than any other focus region. Accordingly, the IOL 11 provides very good visual acuity from distance to intermediate, and provides better visual acuity for objects at infinity than the IOL 13. The IOL 11 may be considered to be particularly adapted for, or even optimized for, distance to intermediate vision.

The lens body 23 of the IOL 13 has a circular outer periphery, an optical axis 38, a circular central zone 37 and optical zones 39, 41, 43 and 45 which are preferably annular and concentric with the central zone 37. All of these zones 37, 39, 41, 43 and 45 are centered on the optical axis 38. The nature of the optical zones 37, 39, 41, 43 and 45 makes the lens body 23 optically different from the lens body 15, but except for this the IOLs 11 and 13 may be identical, if desired.

It can be seen from FIG. 8 that lens body 23 has a second baseline diopter power which is different from the first baseline diopter power of lens body 15. In particular, lens body 23 has a second baseline diopter power which is not for distance vision correction. The second baseline diopter power is more myopic than the first baseline diopter power. Specifically, the second baseline diopter power of lens body 23 is at 1.0 diopter, an intermediate vision connection power. The central zone 37, the annular zone 41 and the outer annular zone 45 are at or about this second baseline diopter power. In this embodiment, the power of the annular zone 41 decreases progressively and slightly from the outer edge of the zone 39 to about the inner edge of the zone 43 to provide spherical aberration correction. Thus, although the optical power of the zone 41 does diminish in a radial outward direction in this fashion, it nevertheless is considered to be at about the second baseline diopter power of lens body 23 needed for intermediate vision correction for the patient. For example, the vision correction power of the zone 41 may decrease from a 1.0 diopters to about 0.75 diopters.

The zones 39 and 43 have vision correction powers which are increased relative to the second baseline diopter power of lens body 23, but the increases are lower than the diopter power required for full near vision correction. Overall, the use of reduced diopter add power in both lens bodies 15 and 23 is effective to advantageously reduce the size and/or intensity of multifocal halos relative to such halos which occur using multifocal lens designs employing full near add powers.

The vision correction power in the zone 39 reduces progressively and slightly in a radial outward direction from an add power such as 2.5 diopters as shown in FIG. 8 to a slightly less add power, for example of about 2.3 diopters, so as to provide for spherical aberration correction. Again, to correct for spherical aberration, the maximum power of the zone 43 is about the minimum power of the zone 39 and reduces progressively and slightly in a radial outward direction as shown in FIG. 8. By way of example, the power of the zone 43 may reduce linearly in a radial outward direction from about 2.3 diopters to about 2.15 diopters.

Looked at from a different perspective, lens body 15 (power curve shown in FIG. 7) and lens body 23 (power curve shown in FIG. 8) have substantially similar, even identical, power curves with the exception of the first baseline diopter power of lens body 15, which is for distance vision correction and the second baseline diopter power of lens body 23 which is 1.0 diopter myoptic.

In this embodiment, the IOL 13 has enhanced intermediate-to-near vision.

From FIGS. 7 and 8, it is apparent that the maximum powers of any region of the IOL 11 and IOL 13 are less than the add power required for full near vision correction, the latter being an add power which typically is greater than 2.5 diopters. Also, the maximum powers of any region of the IOL 11 are no greater than about the intermediate vision correction power. Conversely, the minimum powers of any region for the IOL 13 is no less than about the intermediate vision correction power. The plots of FIGS. 7 and 8 represent power curves showing how the vision correction power of each of the IOLs 11 and 13 changes in a radially outward direction from the optical axes 16 and 38, respectively, and it is apparent that the power curves of FIGS. 7 and 8 are different, particularly with regard to the baseline diopter power of each of the lens bodies 15 and 23. Moreover, this difference in these power curves contributes to the range of vision and visual acuity characteristics of IOLs 11 and 13. Except for this difference in baseline diopter power, the power curve of IOL 11 is substantially similar to the power curve of IOL 13.

FIGS. 1–3 illustrate one way that this invention may be embodied in IOLs. However, the invention may also be embodied in ophthalmic lenses which are adapted to be disposed on or in the cornea such as contact lenses and corneal inlays. The lens bodies 15 and 23 of FIGS. 1 and 2 may also be considered as schematically representing contact lenses or corneal inlays. Of course, these latter two forms of ophthalmic lenses do not have the fixation members 17 or 25.

This invention also provides a method of correcting the vision of a patient which comprises placing first and second multifocal ophthalmic lenses on or in the eyes of a patient with the first lens being distance biased and providing better visual acuity for objects at infinity than the second lens. The second lens may be considered near biased and provides better visual acuity from intermediate-to-near distances than the first lens. The maximum power of the second lens preferably is less the add power required for full near vision correction for the patient. With specific reference to the embodiments shown in FIGS. 1–3, the method includes implanting the IOLs 11 and 13 in the eyes, respectively, of the patient. This implantation may occur with the natural lens in place or may follow the removal of the natural lens from the eye.

In the event the natural lens is removed, IOL 11 is implanted in the capsular bag with the fixation members 17 in contact with the capsular bag. The IOL 13, which has optical characteristics different from the IOL 11, is similarly implanted in the other eye, with the natural lens removed, of the patient.

Figure 11A:
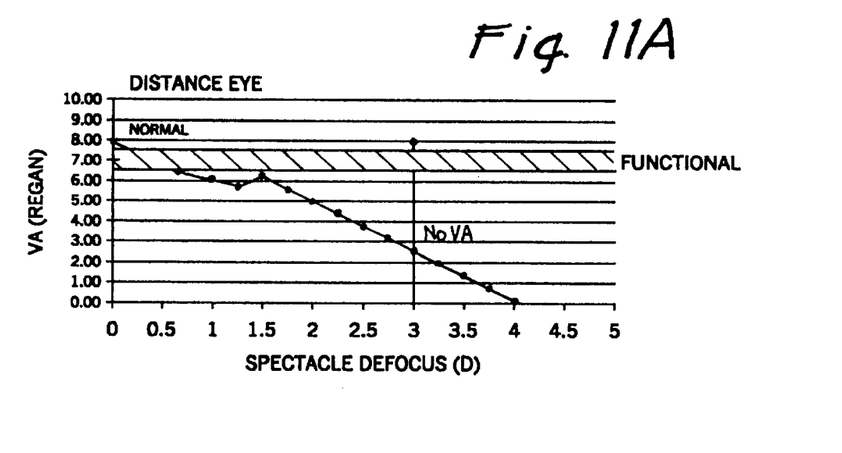
FIG. 11A is a plot of visual acuity versus add power for the IOL of FIG. 1 when implanted in an eye of a patient after removal of the natural lens or in the eye of a phakic patient who is an absolute presbyope with no accommodation.
Figure 11B:
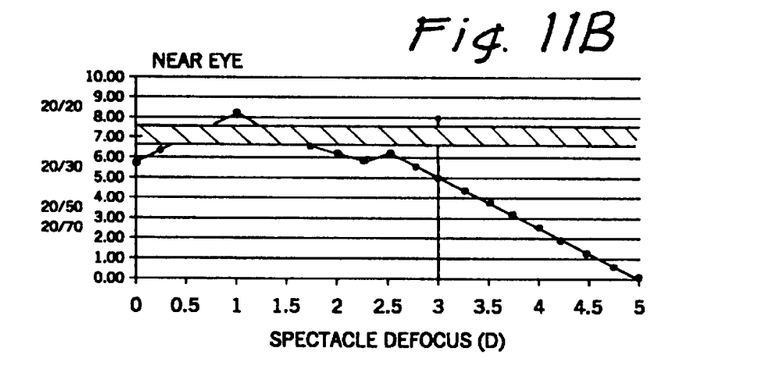
FIG. 11B is a plot similar to FIG. 11A for the IOL of FIG. 2 when implanted in an eye of a patient after removal of the natural lens or in the eye of a phakic patient who is an absolute presbyope with no accommodation.
Figure 11C:
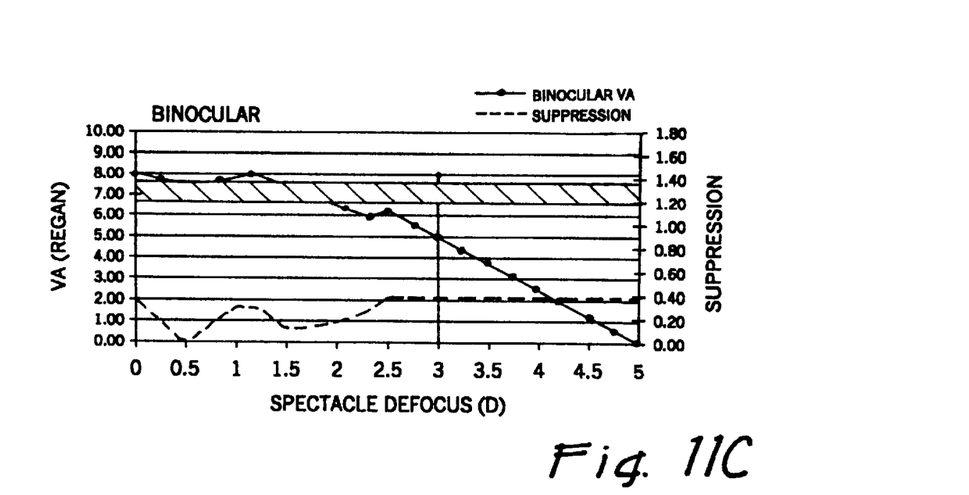
FIG. 11C is a plot similar to FIG. 11A for binocular vision when the IOLs of FIGS. 1 and 2 are implanted in the eyes, respectively, of a patient after removal of the natural lenses or in the eyes, respectively, of a phakic patient who is an absolute presbyope with no accommodation.
Figure 12A:
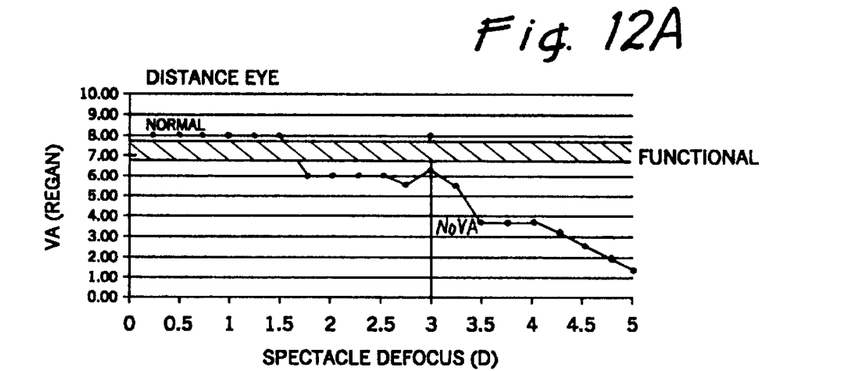
FIG. 12A is a plot of visual acuity versus add power for the IOL of FIG. 1 when implanted in an eye of a phakic patient who is an early presbyope with 1.5 diopters of residual accommodation.
Figure 12B:
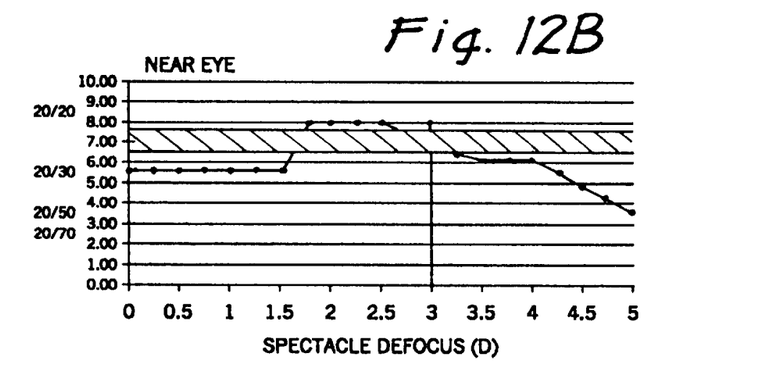
FIG. 12B is a plot of visual acuity versus add power for the IOL of FIG. 2 when implanted in an eye of a phakic patient who is an early presbyope with 1.5 diopters of residual accommodation.

FIGS. 11A–C and 12A–C are of use in gaining a further understanding of how the IOLs 11 and 13 work. FIGS. 11A–C are through-focus-acuity charts for a pseudophakic patient (with no natural accommodation) or a phakic patient who is an absolute presbyope with no accommodation with these IOLs implanted. FIGS. 12A and C are through-focus-acuity charts for a phakic patient who is an early presbyope with 1.5 diopters of residual accommodation with these IOLs implanted. Each of these figures shows visual acuity (VA) along the ordinate and add power in diopters along the abscissa. In addition, the corresponding object distance, the reciprocal of the diopter add power in meters, is also shown along the abscissa. The add power is the add power required by a patient with no accommodation at the corresponding distance indicated on the abscissa. The units for visual acuity or VA are Regan. A visual acuity of about 8 corresponds to 20/20 and is considered normal vision. Functional vision is considered to be about 20/30 up to nearly 20/20, and is shown by the cross hatched or dashed line enclosed band in FIGS. 11A–C and 12A–C. Although functional vision is clinically not normal, it may seem normal to the patient. Below about 20/30 vision becomes progressively more difficult and somewhere about 3 Regan or slightly worse than 20/60 there is essentially no usable visual acuity. The visual acuity plots of FIGS. 11A–C and 12A–C are theoretical.

The IOL 11 (FIGS. 11A and 12A) has better visual acuity at infinity than does the IOL 13 (FIGS. 11B and 12B) as shown by the higher visual acuity at the ordinate. By comparing FIGS. 11A to 11B and FIGS. 12A to 12B, it can be seen that the IOL 13 provides better visual acuity from intermediate to near distance than does IOL 11 and that visual acuity in this range is enhanced. Also, by comparing these figures, it can be seen that the IOL 13 provides better visual acuity for objects at near distances than the IOL 11.

The binocular visual acuity remains functional or better for distance and intermediate objects. In addition, near reading between 40 centimeters and 33 centimeters is functional or better. Thus, the patients should perform all tasks well.

Another important benefit of the use of different IOLs 11 and 13 relates to suppression. As used herein, "suppression" is defined as the between-eye-visual acuity difference normalized to the visual acuity difference for a monovision patient with 2.5 diopters of prescription disparity. A suppression level of 1.0 indicates a full monovision visual acuity difference. It is believed, based on a brief review of the literature, that a majority of patients will not tolerate a suppression of 1.0. However, approximately 50% of the patients will tolerate a suppression level of 0.6.

Figure 12C:
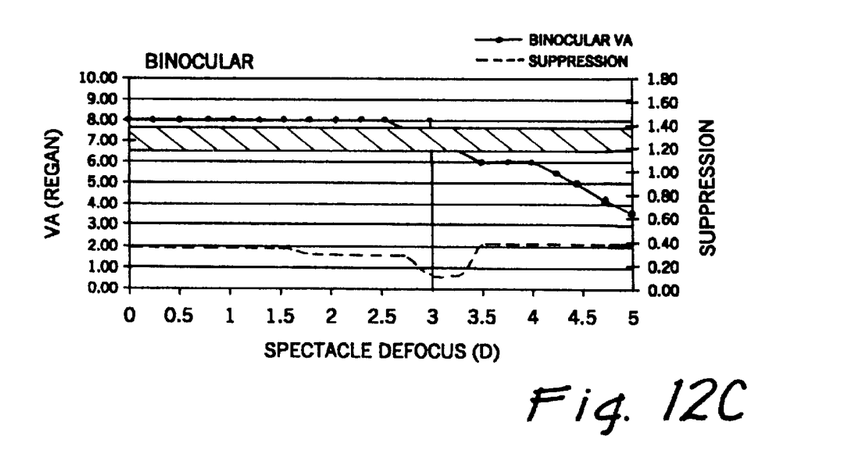
FIG. 12C is a plot of visual acuity versus add power for the IOLs of FIG. 1 and 2 when implanted in the eyes, respectively, of a phakic patient who is an early presbyope with 1.5 diopters of residual accommodation.

FIGS. 11c and 12c include a graph of suppression for IOLs 11 and 13. These IOLs when used together provide a suppression level of 0.4 or less, which is advantageously likely to be well tolerated by a substantial majority of the patients.

FIG. 4 shows a distance-to-intermediate multifocal IOL 111 and FIG. 5 shows an intermediate-to-near multifocal IOL 113 which together with the IOL 111 form a lens pair or ophthalmic lens system for enhancing the vision of a patient. The IOL 111 includes a multifocal lens body or optic 115, an optical axis 116 and has powers for a vision correction as described more fully hereinbelow. The IOL 111 also includes generally radially extending footplate-type fixation members 117 and 118 which, in this embodiment, are integral with the lens body 115 such that the IOL 111 is one piece.

If the IOL 111 is to be implanted without removal of the natural lens from the eye, i.e. in an early presbyope, then the fixation members 117 and 118 should be of a configuration and construction which allow the IOL 111 and the natural lens of the eye to usefully coexist in the eye. In that regard, the configuration shown in FIG. 4 may be employed. The IOL may be fixated to the iris of the eye, may be located in the anterior chamber of the eye and/or may be fixated at the sulcus of the eye. The fixation members 117 and 118 may be made of materials of construction, such as polymeric materials, for example, acrylic, polypropylene, silicone, polymethylmethacrylate and the like, many of which are conventionally used in fixation members. In the embodiment shown each of the fixation members 117 and 118 has the form shown by way of example in FIGS. 4 and 6, and this adapts the IOL 111 for implantation in the anterior chamber of the eye without removal of the natural lens.

As shown in FIG. 6, the lens body 115 has a convex anterior surface 119 and a substantially plano posterior surface 121; however, these configurations are merely illustrative. Although the vision correction power may be placed on either of the surfaces 119 or 121, in this embodiment, the anterior surface 119 is appropriately shaped to provide the desired vision correction powers.

The IOL 113 similarly has a multifocal lens body 123 and fixation members 125 and 126 suitably joined to the lens body 123. The optical characteristics and, in particular the baseline diopter powers, of the lens bodies 115 and 123 are different as described more specifically hereinbelow. However, except for the optical characteristics of the lens bodies 115 and 123, the IOLs 111 and 113 may be identical.

With respect to optical characteristics, it can be seen from FIG. 4 that the IOL 111 has a central zone 127 and additional optical zones 129, 131, 133 and 135. In this embodiment, the central zone 127 is circular and the lens body 115 has a circular outer periphery. Also, in this embodiment, the additional optical zones 129, 131, 133 and 135 are annular and concentric with the central zone 127, and all of these zones are centered on the optical axis 116.

Figure 9:
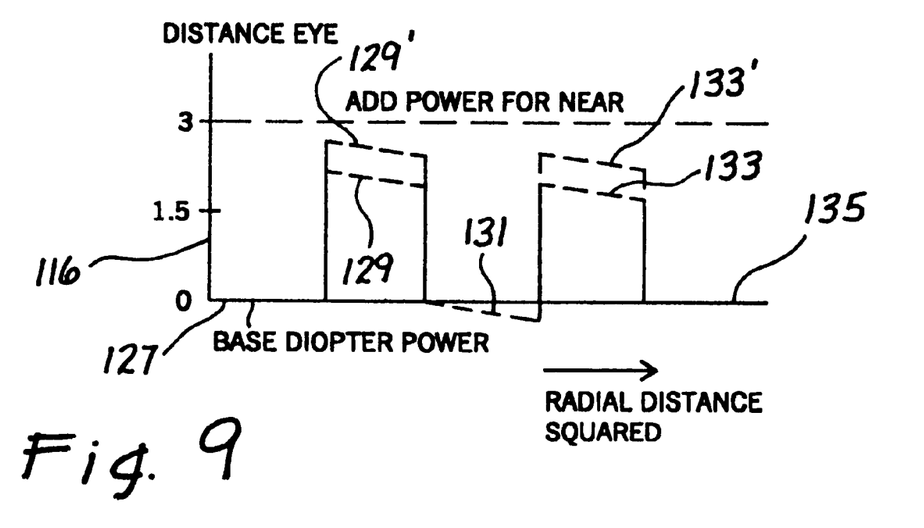
FIG. 9 is a plot similar to FIG. 7 for the IOL of FIG. 4.
Figure 10:
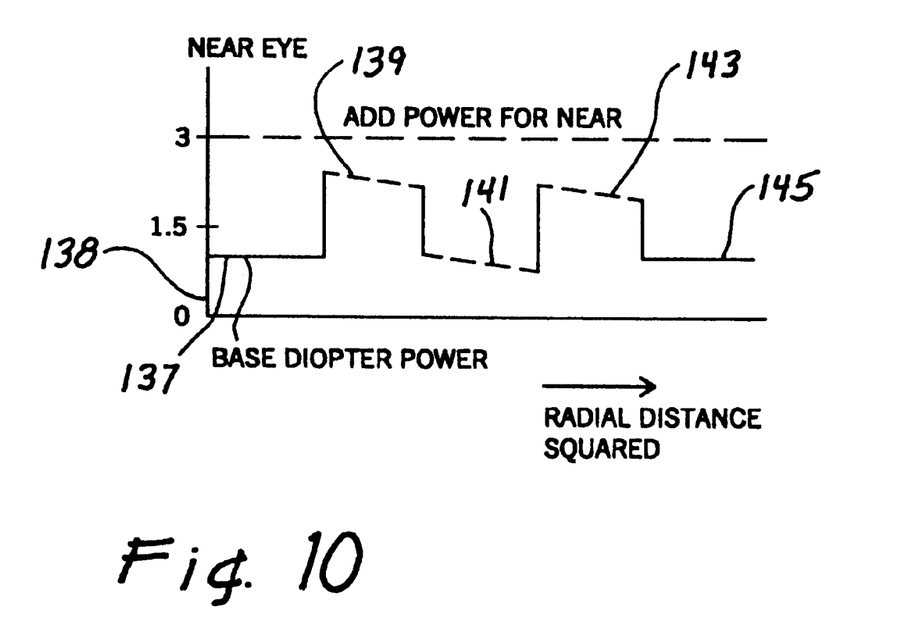
FIG. 10 is a plot similar to FIG. 9 for the IOL of FIG. 5.

With reference to FIG. 9, it can be seen that the central zone 127 and the outermost annular zone 135 have a base diopter power which is the power required by the patient for distance vision correction and is considered as a zero add power. It should also be noted that the diopter power variation shown in FIGS. 9 and 10 is applicable to any point on the surface of the lens bodies 115 and 123, respectively, at a fixed radial distance from the associated optical axes. In other words, the power at any given radial distance from the optical axis 116 is the same, and the power at any given radial distance from the optical axis 138 is the same.

The annular zone 131 has about the first baseline diopter power required for distance vision correction. Although the annular zone 131 could have precisely the power required for distance vision correction, i.e. zero add power, in this embodiment, the power of the annular zone 131 decreases progressively and slightly from the outer edge of the zone 129 to about the inner edge of the zone 133 to provide spherical aberration correction. Thus, although the optical power of the zone 131 does diminish in a radial outward direction in this fashion, it nevertheless is considered to be about the power needed for far or distance vision correction for the patient. For example, the vision correction power of the zone 131 may decrease from a zero add power to about 0.25 diopter below the base diopter power.

The zones 129 and 133 have greater vision correction power than the zones 127, 131 and 135 and are preferably at or about the power required for intermediate vision correction. More broadly, however, the intermediate vision correction power may be taken to embrace a zone of from about 0.5 diopter to about 1.75 diopters. When thus considered, the power of the zones 129 and 133 would all be add powers for about intermediate vision correction. In addition, the add power of zones 129 and 133 are somewhat greater than the add powers of zones 29 and 33 (FIG. 7), respectively.

If desired, the zone 129 and 133 can have optical powers approaching add powers required for full near vision correction. This embodiment is shown in the shadow or dotted lines in FIG. 9, with the zones shown as 129' and 133'. Such a higher add power embodiment is advantageous for patients who require near vision correction, even at the expense of the presence or occurrence of halos and other nighttime images of somewhat increased size and/or intensity.

The vision correction power in the zone 129 reduces progressively and slightly in a radial outward direction from an add power for intermediate vision correction such as about 2 diopters as shown in FIG. 9 to a slightly less add power for intermediate vision correction so as to provide for spherical aberration correction. Again, to correct for spherical aberration, the maximum power of the zone 133 is about the minimum power of the zone 129 and reduces progressively and slightly in a radial outward direction as shown in FIG. 9. By way of example, the power of the zone 129 may decrease linearly from about 2 diopters to about 1.8 diopters and the vision correction power of the zone 133 may reduce linearly in a radial outward direction from about 1.8 diopters to about 1.55 diopter. Thus, all of the powers of the zones 129 and 133 may be considered as add powers for near or intermediate vision correction.

The annular areas of the distance correction zones 127, 131 and 135 are intended to be larger than the annular areas of the intermediate power zones 129 and 133. Moreover, there are three of the distance power zones 127, 131 and 135 and only two of the near or intermediate vision correction zones 129 and 133, although other numbers of these zones may be employed, if desired. Thus, a larger surface of the lens body 115 is dedicated to focusing or directing light to a far focus region than any other focus region. Accordingly, the IOL 111 provides very good visual acuity from distance to intermediate, and provides better visual acuity for objects at infinity than the IOL 113. The IOL 111 may be considered to be particularly adapted for, or even optimized for, distance-to-intermediate vision.

The lens body 123 of the IOL 113 has a circular outer periphery, an optical axis 138, a circular central zone 137 and optical zones 139, 141, 143 and 145 which are preferably annular and concentric with the central zone 137. All of these zones 137, 139, 141, 143 and 145 are centered on the optical axis 38. The nature of the optical zones 137, 139, 141, 143 and 145 makes the lens body 123 optically different from the lens body 115, but except for this the IOLs 111 and 113 may be identical, if desired.

It can be seen from FIG. 10 that the lens body 123 has a second baseline diopter power which is different from the first baseline diopter power of lens body 115. In particular, lens body 123 has a second baseline diopter power which is not for distance vision correction. The second baseline diopter power is more myopic than the first baseline diopter power. Specifically, the second baseline diopter power of lens body 123 is at 1.0 diopters, intermediate vision correction power. The center zone 137, the annular zone 141 and the outer annular zone 145 are at or about this second baseline diopter power. In this embodiment, the power of the annular zone 141 decreases progressively and slightly from the outer edge from the zone 139 to about the inner edge of the zone 143 to provide spherical aberration correction. Thus, although the optical power of the zone 141 does diminish in a radial outward direction in this fashion, it nevertheless is considered to be at about the second baseline diopter power of lens body 123 needed for intermediate vision correction for the patient.

The zones 139 and 143 have vision correction powers which are increased relative to the second baseline diopter power of lens body 123, but are lower than the diopter power required for full near vision correction. The use of reduced diopter add powers in both lens bodies 115 and 123 is effective to advantageously reduce the size and/or intensity of multifocal halos relative to such halos which occur using multifocal lens designs employing full near diopter add powers. The add powers of zones 139 and 143 relative to the second baseline diopter power of lens body 123 are different, in particular reduced, compared to the add powers of zones 129 and 133 relative to the first baseline diopter 115. These features of lens bodies 115 and 123 distinguish them from lens bodies 15 and 23 (FIGS. 7 and 8) in which, except for the difference in baseline diopter powers, the power curves of lens bodies 15 and 23 are substantially similar.

The vision correction power of the zone 139 reduces progressively and slightly in a radial outward direction from an add power such as 2.5 diopters as shown in FIG. 10 to a slightly less add power, for example of about 2.3 diopters so as to provide for spherical aberration correction. Again, to correct for spherical aberration, the maximum power of the zone 143 is about the minimum power of the zone 139 and reduces progressively and slightly in a radial outward direction as shown in FIG. 10. By way of example, the power of the zone 143 may reduce linearly in a radial outward direction from about 2.3 diopters to about 2.15 diopters.

In this embodiment, the IOL 113 has enhanced intermediate-to-near vision.

The plots in FIGS. 9 and 10 represent power curves showing how the vision correction power of each of the IOLs 111 and 113 changes in a radially outward direction from the optical axis 116 and 138, respectively, and it is apparent that the power curves of FIGS. 9 and 10 are different, particularly with regard to the baseline diopter power of each of the lens bodies 115 and 123. The differences in these power curves contribute to the range of vision and vision acuity characteristics of IOLs 111 and 113.

It should be noted that the lens bodies 115 and 123 of FIGS. 4 and 5 may also be considered as schematically representing contact lens or corneal inlays. Of course these latter two forms of ophthalmic lenses do not have the fixation members 117 or 125.

The IOLs 111 and 113 are particularly adapted to be implanted in anterior chambers of eyes.

Figure 13A:
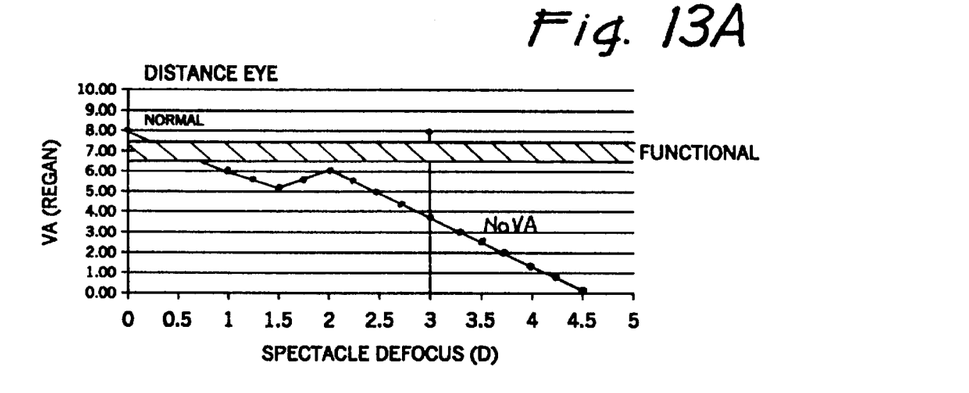
FIG. 13A is a plot of visual acuity versus add power for the IOL of FIG. 4 when implanted in an eye of a patient after removal of the natural lens or in the eye of a phakic patient who is an absolute presbyope with no accommodation.
Figure 13B:
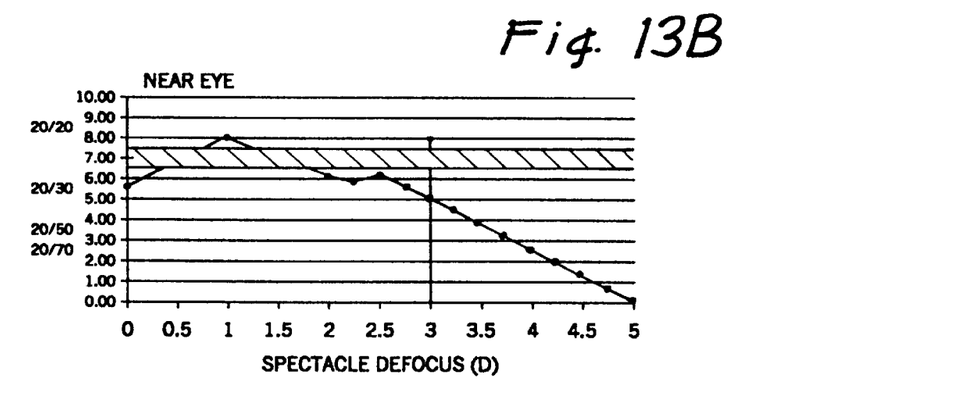
FIG. 13B is a plot similar to FIG. 13A for the IOL of FIG. 5 when implanted in an eye of a patient after removal of the natural lens or in the age of a phakic patient who is an absolute presbyope with no accommodation.
Figure 13C:
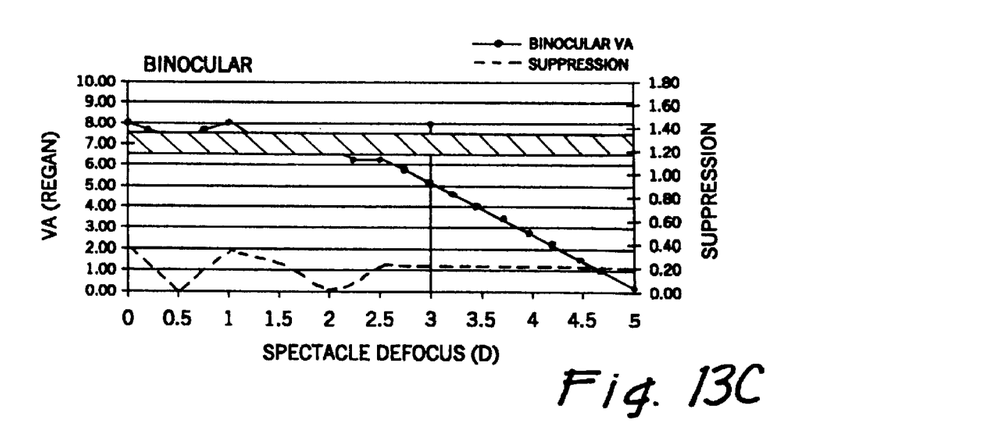
FIG. 13C is a plot similar to FIG. 13A for binocular vision when the IOLs of FIGS. 4 and 5 are implanted in the eyes, respectively, of a patient after removal of the natural lenses or in the eyes, respectively, of a phakic patient who is an absolute presbyope with no accommodation.

FIGS. 13a–c are of use in gaining a further understanding of how the IOLs 111 and 113 work. FIGS. 13a–c are through-focus acuity charts for a pseudophakic patient, with no natural accommodation, or a phakic patient who is an absolute presbyope with no accommodation, with these IOLs implanted.

The IOL 111 (FIG. 13a) has better vision acuity at infinity than does the IOL 113 (FIG. 13b) as shown by the higher vision acuity at the ordinate. By comparing FIG. 13a to 13b, it can be seen that IOL 113 provides better vision acuity for intermediate to near distances than does IOL 111 and that vision acuity in this range is enhanced.

The binocular vision acuity remains functional or better for distance and intermediate objects. In addition, near reading between 40 cm and 33 cm is acceptable. Thus the patients should perform all tasks well.

In addition, the suppression level shown in FIG. 13c is, overall, reduced relative to the suppression levels obtained using the combination of IOLs 11 and 13 (see FIGS. 11c and 12c). This reduced suppression level of the combination of IOLs 111 and 113 is believed to result from the difference in add powers between lens bodies 115 and 123. As noted previously, the add powers, relative to the baseline diopter powers, of lens bodies 15 and 23 are substantially similar. The reduced suppression level shown in FIG. 13c indicates that the combination of IOLs 111 and 113 is advantageously likely to be well tolerated by a large majority of the patients.

While this invention has been described with respect to various specific examples and embodiments, it is to be understood that the invention is not limited thereto and that it can be variously practiced within the scope of the following claims.

What is claimed is:

1. An ophthalmic lens system for improving the vision of a patient comprising:
   a first multifocal ophthalmic lens for use with one eye of a patient, and having a first baseline diopter power for distance vision correction;
   a second multifocal ophthalmic lens for use with the other eye of the patient, and having a second baseline diopter power for other than distance vision correction and a maximum power less than the add power required for full near vision correction for the patient; and
   each of said first and second lenses being adapted for implantation in an eye or to be disposed on or in a cornea of an eye.

2. An ophthalmic lens system as defined in claim 1 wherein the second baseline diopter power is more myopic than the first baseline power.

3. An ophthalmic lens system as defined in claim 1 wherein the second baseline diopter power is for intermediate vision correction.

4. An ophthalmic lens system as defined in claim 1 wherein at least one of the first lens and the second lens has a power including an intermediate add power for intermediate vision correction for the patient and a maximum add power which is less than the add power required for full near vision correction for the patient.

5. An ophthalmic lens system as defined in claim 4 wherein the maximum add power of any region of the second lens is no greater than about the intermediate add power.

6. An ophthalmic lens system as defined in claim 4 wherein the maximum add power of any region of the first lens is no greater than about the intermediate add power.

7. An ophthalmic lens system as defined in claim 1 wherein both the first lens and the second lens have a maximum add power which is less than the add power required for full near vision correction for the patient.

8. An ophthalmic lens system as defined in claim 1 wherein the second lens provides better visual acuity from intermediate to near distances than the first lens.

9. An ophthalmic lens system as defined in claim 1 wherein each of the first and second lenses has an optical axis, the power of each of the first and second lenses changes along a power curve in a radially outward direction from the associated optical axis and the power curve for the first lens is substantially similar to the power curve for the second lens.

10. An ophthalmic lens as defined in claim 1 wherein each of the first and second lenses has an optical axis, the power of each of the first and second lenses changes along a power curve in a radially outward direction from the associated optical axis and the power curve for the first lens is different from the power curve of the second lens.

11. An ophthalmic lens system as defined in claim 10 which provides a reduced level of suppression relative to a similar lens combination with lenses having substantially similar power curves.

12. An ophthalmic lens system as defined in claim 1 wherein the first lens provides better visual acuity for objects at infinity than the second lens.

13. An ophthalmic lens system as defined in claim 1 wherein the second lens has a zone with an intermediate add power for intermediate vision correction and the zone has optical aberrations which increase the depth of focus of the zone.

14. An ophthalmic lens system as defined in claim 13 wherein the zone extends radially outwardly and has progressively increasing powers as the zone extends radially outwardly.

15. An ophthalmic lens system as defined in claim 1 wherein the first and second lenses are intraocular lenses.

16. An ophthalmic lens system as defined in claim 1 wherein the first and second lenses are selected from the group consisting of contact lenses and corneal inlays.

17. An ophthalmic lens system for improving the vision of a patient comprising:
a first multifocal ophthalmic lens for use with one eye of a patient, the first lens having a power including a first baseline diopter power for distance vision correction for the patient;
a second multifocal ophthalmic lens for use with the other eye of the patient, the second lens having a second baseline diopter power other than for distance vision correction, a power including an intermediate add power for intermediate vision correction for the patient and a maximum power which is less than the full add power required for near vision correction for the patient;
the first lens providing better visual acuity for objects at infinity than the second lens; and
each of the first and second lenses being adapted for implantation in an eye or to be disposed on or in a cornea of an eye.

18. An ophthalmic lens system as defined in claim 17 wherein the second baseline diopter power is more myopic than the first baseline diopter power.

19. An ophthalmic lens system as defined in claim 17 wherein the second baseline diopter power is for intermediate vision correction.

20. An ophthalmic lens system as defined in claim 17 wherein the maximum add power of any region of the second lens is no greater than about the intermediate add power.

21. An ophthalmic lens system as defined in claim 17 wherein the maximum add power of any region of the first lens is less than the full add power required for near vision correction for the patient.

22. An ophthalmic lens system as defined in claim 17 wherein the maximum add power of any region of the first lens is no greater than about the intermediate add power.

23. An ophthalmic lens system as defined in claim 17 wherein the second lens is biased for near vision correction for the patient.

24. An ophthalmic lens system as defined in claim 17 wherein each of the first and second lenses has an optical axis, the power of each of the first and second lenses changes along a power curve in a radially outward direction from the associated optical axis and the power curve for the first lens is substantially similar to the power curve for the second lens.

25. An ophthalmic lens as defined in claim 17 wherein each of the first and second lenses has an optical axis, the power of each of the first and second lenses changes along a power curve in a radially outward direction from the associated optical axis and the power curve for the first lens is different from the power curve of the second lens.

26. An ophthalmic lens system as defined in claim 25 which provides a reduced level of suppression relative to a similar lens combination in which the power curves of the first and second lens are substantially similar.

27. The ophthalmic lens systems as defined in claim 17 wherein the first and second lenses are intraocular lenses.

28. An ophthalmic lens system as defined in claim 17 wherein the first and second lenses are selected from the group consisting of contact lenses and corneal inlays.

29. An ophthalmic lens system for improving the vision of a patient comprising:
a first multifocal lens for use with one eye of the patient, the first lens having a first optical axis and a first baseline diopter power for distance vision correction, the power of the first lens changes along a first power curve in a radially outward direction from the first optical axis;
a second multifocal lens for use with the other eye of the patient, the second lens having a second optical axis and a second baseline diopter power for other than distance vision correction, the power of the second lens changes along a second power curve in a radially outward direction from the second optical axis;
the first and second power curves being substantially similar; and
each of the first and second lenses being adapted for implantation in an eye or to be disposed on or in a cornea of an eye.

30. An ophthalmic lens system of claim 29 wherein the maximum add power of any region of the second lens is less than the full add power required for near vision; and the first lens providing better visual acuity for objects at infinity than the second lens and the second lens providing better visual acuity from intermediate to near distance than the first lens.

31. An ophthalmic lens system as defined in claim 29 wherein the second baseline diopter power is more myopic than the first baseline power.

32. An ophthalmic lens system as defined in claim 29 wherein the second baseline diopter power is for intermediate vision correction.

33. An ophthalmic lens system as defined in claim 29 wherein the best visual acuity provided by the second lens is for objects at intermediate distances.

34. An ophthalmic lens system as defined in claim 29 wherein the first and second lenses are intraocular lenses.

35. An ophthalmic lens system as defined in claim 29 wherein the first and second lenses are selected from the group consisting of contact lenses and corneal inlays.

36. An ophthalmic lens system for improving the vision of a patient comprising:
a first multifocal ophthalmic lens for use with one eye of a patient, the first lens having a first baseline diopter power and being biased for distance vision;
a second multifocal ophthalmic lens for use with the other eye of the patient, the second lens having a second baseline diopter power different from the first baseline diopter power and a maximum power less than the add power required for full near vision correction for the patient, and being biased for intermediate vision; and each of the first and second lenses being adapted for implantation in an eye or to be disposed on or in the cornea.

37. An ophthalmic lens system as defined in claim 36 wherein each of said lenses is an intraocular lens.

38. An ophthalmic lens system as defined in claim 36 wherein the first and second lenses are selected from the group consisting of contact lenses and corneal inlays.

* * * * *